United States Patent [19]

Wallquist et al.

[11] Patent Number: 4,810,802
[45] Date of Patent: Mar. 7, 1989

[54] PROCESS FOR THE PREPARATION OF BROMINATED PYRROLO-[3,4-C]-PYRROLES AND MIXTURES THEREOF

[75] Inventors: Olof Wallquist, Marly; Abul Iqbal, Ettingen, both of Switzerland; Johannes Pfenninger, Wilmington, Del.; Alain C. Rochat, Fribourg, Switzerland

[73] Assignee: Ciba-Geigy Corporation, Ardsley, N.Y.

[21] Appl. No.: 7,836

[22] Filed: Jan. 27, 1987

[30] Foreign Application Priority Data

Jan. 31, 1986 [CH] Switzerland ............. 365/86

[51] Int. Cl.$^4$ .......................................... G07D 487/04
[52] U.S. Cl. ................................................. 548/453
[58] Field of Search ........................ 548/453; 260/694

[56] References Cited

U.S. PATENT DOCUMENTS

| | | | |
|---|---|---|---|
| 3,592,947 | 7/1971 | Stein | 260/694 |
| 4,415,685 | 11/1983 | Iqbal et al. | 524/92 |
| 4,490,562 | 12/1984 | Schreiber et al. | 568/637 |
| 4,579,949 | 4/1986 | Rochat et al. | 548/453 |
| 4,585,878 | 4/1986 | Jost et al. | 548/453 |

OTHER PUBLICATIONS

Glinzer & Fittig, Ann. 136, 301–303 (1865).
Hubner et al., Ann. 154, 293–303 (1870).
Chem. Abst., vol. 63, 8272 (1965).

Primary Examiner—David B. Springer
Attorney, Agent, or Firm—Harry Falber; Edward McC. Roberts

[57] ABSTRACT

Process for the preparation of brominated pyrrolo-[3,4-c]pyrrole pigments by bromination of a pyrrolo-[3,4-c]-pyrrole or of a mixture of different pyrrolo-[3,4-c]-pyrroles of the formula I

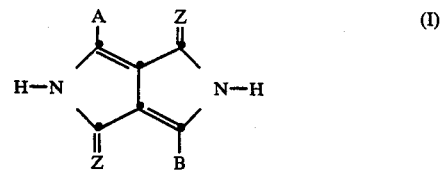

with an amount of a brominating agent which supplies 0.5 to 70 equivalents of bromine, with or without a solvent, and subsequent isolation of the brominated pyrrolo-[3,4-c]-pyrrole by removal of the excess brominating agent and, if appropriate, the solvent by customary methods.

The desired brominated pyrrolo-[3,4-c]pyrroles are obtained directly in a high yield by this process.

Reference is made to claim 1 in respect of the meaning of substituents A, B and Z.

14 Claims, No Drawings

PROCESS FOR THE PREPARATION OF BROMINATED PYRROLO-[3,4-C]-PYRROLES AND MIXTURES THEREOF

The present invention relates to a process for the preparation of brominated pyrrolo-[3,4-c]-pyrroles by direct bromination of pyrrolo-[3,4-c]-pyrroles.

Brominated 1,4-diketo-pyrrolo-[3,4-c]-pyrroles, such as are described, for example, in European Pat. No. A-61,426 are an important group of pigments of the new class of 1,4-diketo-pyrrolo-[3,4-c]-pyrroles. They have hitherto been prepared from the corresponding brominated nitriles by reaction with ethylbromoacetate and zinc in accordance with the method described in European Pat. No. A-61,426, or with a succinic acid diester in the presence of a strong base, in accordance with the method described in European Pat. No. A-94,911. The brominated nitriles required for the preparation of the 1,4-diketo-pyrrolo-[3,4-c]-pyrroles brominated on the aromatic substituent are difficult to obtain directly from the aromatic nitriles by bromination, but must be prepared from simple starting materials in multi-stage processes with low yields and relatively high costs. Thus, for example, benzonitrile cannot be converted easily and directly into p-bromobenzonitrile with bromine. p-Bromobenzonitrile is prepared by bromination of toluene (Glinzer & Fittig, Ann. 136, 301 (1865)) and subsequent oxidation to the nitrile (Hübner & Wallach, Ann. 154, 293 (1870); and German Offenlegungsschrift No. 1,189,976)

Brominated nitriles such as are required for the known preparation of brominated 1,4-diketo-pyrrolo-[3,4-c]-pyrroles are therefore accessible with difficulty and only via several stages at high costs.

It has now been found that, surprisingly, 3,6-diaryl-1,4-diketo-pyrrolo-[3,4-c]-pyrroles which are substituted by bromine on the aromatic substituent can be prepared in a high yield by direct bromination of the corresponding 1,4-diketopyrrolo-[3,4-c]-pyrroles, which are easily obtainable from nitriles which are usually inexpensive and are readily accessible.

The present invention accordingly relates to a process for the preparation of bromine-substituted 3,6-diaryl-1,4-diketo-pyrrolo-[3,4-c]-pyrroles by bromination of a pyrrolo-[3,4-c]-pyrrole or a mixture of different pyrrolo[3,4-c]-pyrroles of the formula I

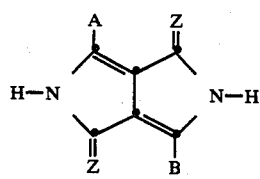
(I)

in which A and B are identical or different isocyclic aromatic radicals and Z is oxygen or sulfur, with a brominating agent in an amount which supplies 0.5 to 70 equivalents of bromine, with or without a solvent, and subsequent isolation of the brominated pyrrolo-[3,4-c]-pyrrole by removal of the excess brominating agent and, if necessary, of the solvent by customary methods.

A single pyrrolo-[3,4-c]-pyrrole is preferably used as the starting substance. Z is preferably oxygen.

The radicals A ad B are preferably identical.

Isocyclic aromatic radicals A and B are preferably mono-, di-, tri- or tetracyclic, in particular mono- or bicyclic radicals, for example phenyl, biphenylyl or naphthyl. The isocyclic aromatic radicals can contain customary substituents which do not confer water-solubility, for example: halogen, nitro, amino, carbamoyl, cyano, trifluoromethyl $C_2$–$C_{13}$-alkylcarbamoyl, $C_1$–$C_{12}$-alkyl, $C_1$–$C_{12}$-alkoxy, $C_1$–$C_{12}$-alkylmercapto, $C_2$–$C_{13}$-alkoxycarbonyl, $C_2$–$C_{13}$-alkanoylamino, $C_1$–$C_{12}$-monoalkylamino, $C_2$–$C_{24}$-dialkylamino, mono-($C_5$–$C_7$-cycloalkyl)-amino, di-($C_5$–$C_7$-cycloalkyl)-amino, phenyl which is unsubstituted or substituted by halogen, $C_1$–$C_{12}$-alkyl or $C_1$–$C_{12}$-alkoxy, phenoxy, phenylmercapto, phenoxycarbonyl, phenylcarbamoyl or benzoylamino.

Examples of $C_2$–$C_{13}$-alkylcarbamoyl groups are N-methylcarbamoyl, N-ethylcarbamoyl, N,N-dimethylcarbamoyl, N-butylcarbamoyl, N,N-dibutylcarbamoyl and N,N-dihexylcarbamoyl.

Examples of $C_1$–$C_{12}$-alkyl groups are methyl, ethyl, n-propyl, isopropyl, n-butyl, sec-butyl, tert.-butyl, tert.-amyl, n-pentyl, n-hexyl, 1,1,3,3-tetramethylbutyl, n-heptyl, n-octyl, nonyl, decyl, undecyl and dodecyl.

Examples of $C_1$–$C_{12}$-alkoxy groups are: methoxy, ethoxy, propoxy, isopropoxy, n-butoxy, sec-butoxy, tert.-butoxy, n-pentyloxy, tert.-amyloxy, n-hexyloxy, n-heptyloxy, n-octyloxy, decyloxy and dodecyloxy.

Examples of $C_1$–$C_{12}$-alkylmercapto are methylmercapto, ethylmercapto, propylmercapto, butylmercapto, n-pentylmercapto, tert.-amylmercapto, n-hexylmercapto, decylmercapto and dodecylmercapto.

Examples of $C_2$–$C_{13}$-alkoxycarbonyl groups are methoxy-, ethoxy-, propoxy-, isopropoxy-, n-butoxy-, tert.-butoxy-, n-hexyloxy-, n-octyloxy- and dodecyloxy-carbonyl.

Examples of $C_2$–$C_{13}$-alkanoylamino are acetylamino, propionylamino and butyrylamino.

Examples of $C_1$–$C_{12}$-monoalkylamino are methylamino, ethylamino, isopropylamino and n-butylamino.

An example of mono-($C_5$–$C_7$-cycloalkyl)-amino is cyclohexylamino.

Examples of $C_1$–$C_{12}$-dialkylamino are dimethylamino, diethylamino, dibutylamino and dihexylamino.

An example of di-($C_5$–$C_7$-cycloalkyl)-amino is dicyclohexylamino.

The bromination of pyrrolo-[3,4-c]-pyrroles of the formula I in which A and B are phenyl or naphthyl which is unsubstituted or substituted by the customary substituents which do not confer water-solubility is of particular interest.

The bromination of pyrrolo-[3,4-c]-pyrroles of the formula I in which A and B are a group of the formula

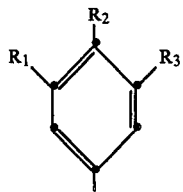

in which $R_1$, $R_2$ and $R_3$ independetly of one another are hydrogen, halogen, nitro, amino, carbamoyl, cyano, trifluoromethyl, $C_2$-$C_{13}$-alkylcarbamoyl, $C_1$-$C_{12}$-alkyl, $C_1C_{12}$-alkoxy, $C_1$-$C_{12}$-alkylmercapto, $C_2$-$C_{13}$-alkoxycarbonyl, $C_2$-$C_{13}$-alkanoylamino, $C_1$-$C_{12}$-monoalkylamino, $C_2$-$C_{24}$-dialkylamino, phenyl which is unsubstituted or substituted by halogen, $C_1$-$C_{12}$-alkyl or $C_1$-$C_{12}$ alkoxy, phenoxy, phenylmercapto, phenoxycarbonyl or phenylcarbamoyl, and in which at least one of the substituents $R_1$, $R_2$ or $R_3$ must be hydrogen, is of special interest.

The bromination of pyrrolo-[3,4-c]-pyrroles of the formula I in which A and B are a group of the formula

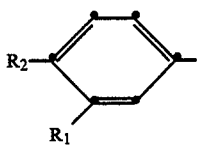

in which $R_1$ and $R_2$ are hydrogen, $C_1$-$C_4$-alkyl, $C_1$-$C_4$-alkoxy or phenyl, is preferred.

The bromination of pyrrolo-[3,4-c]-pyrroles of the formula I in which A and B are a group of the formula

in which $R_2$ is hydrogen or phenyl, is particularly preferred.

The bromination of 1,4-diketopyrrolo-[3,4-c]pyrroles of the formula I in which A and B are unsubstituted phenyl is especially preferred.

The 1,4-diketopyrrolo-[3,4-c]-pyrroles to be brominated are known, for example, from European Pat. No. A-61,426, European Pat. No. A-94,911 and European Pat. No. A-133,156 and can be prepared by the methods described in the same publications.

The 1,4-diketopyrrolo-[3,4-c]-pyrrole to be brominated can be brominated with the desired amount of the brominating agent, i.e. in an amount which supplies 0.5 to 70, preferably 2 to 40, equivalents of bromine, either in a solvent or in a melt or in the absence of a solvent at temperatures which can advantageously be varied between −20° and 200° C., preferably between 20° and 150° C., in an open or closed vessel until the desired bromine content is reached.

Examples of suitable brominating agents are: bromine, N-bromosuccinimide, dibromocyanuric acid, thionyl bromide, alkali metal hypobromides, N,N-dibromophenylsulfonamide, pyridine hydrobromide perbromide and N-bromophthalimide. Bromine and dibromocyanuric acid are preferred.

Examples of solvents which can be used are halogenated or nitrated aromatic hydrocarbons, unsubstituted or halogenated aliphatic hydrocarbons and mineral acids. Examples here are: o-dichlorobenzene, nitrobenzene, carbon tetrachloride, 1,1,2,2-tetrachloroethane, methylene chloride, trichloroethylene, tetrachloroethylene, petroleum ether, nitroethane, hexane, decalin, ®Shellsol TD (a mixture of aliphatic hydrocarbons from Shell) and sulfuric acid.

In order to accelerate the bromination, the reaction is advantageously carried out in the presence of a weak base, for example $K_2CO_3$. Surface-active agents, for example polyoxyethylene lauryl ether and the sodium salt of bis-2-ethylhexylsulfosuccinate, as well as oxidizing agents, for example cerium-IV ammonium nitrate and copper-II nitrate, can also advantageously be added.

The bromination of 1,4-diketopyrrolo-[3,4-c]-pyrroles of the formula I is preferably carried out with 2–40 equivalents of bromine in one of the abovementioned solvents or in a mixture thereof or in liquid or gaseous bromine without a solvent, or with dibromocyanuric acid in sulfuric acid, at temperatures between 20° and 150° C. If necessary, the excess bromine is collected by adding a suitable reagent and the suspension is filtered with suction. The residue is advantageously purified in a polar organic solvent and dried in a vacuum drying cabinet.

By choosing the reaction temperature and time and/or the solvent used and/or by increasing or reducing the amount of brominating agent, it is possible to control the process according to the invention so that single products or mixtures of non-brominated and uniformly or differently brominated or of differently brominated 1,4-diketopyrrolo-[3,4-c]-pyrroles are formed.

As a rule, the brominated 1,4-diketo-pyrrolo-[3,4-c]pyrroles obtained according to the invention are used as pigments for colouring high molecular weight organic materials. The pigments can generally be employed directly in the form in which they are obtained by the process according to the invention.

Depending on the nature of their substituents and of the polymers to be coloured, the 1,4-diketopyrrolo-[3,4-c]pyrroles of the formula I, brominated according to the invention, can also be used as polymer-soluble dyes.

The brominated 1,4-diketo-pyrrolo-[3,4-c]-pyrroles prepared according to the present invention are distinguished in particular by a good stability to heat.

Depending on their intended use, it may be advantageous to employ the mixtures, obtainable according to the invention, of brominated and non-brominated or of differently brominated 1,4-diketo-pyrrolo-[3,4-c]-pyrroles.

The mixtures of brominated 1,4-diketo-[3,4-c]-pyrroles which are obtained from compounds of the formula I, in which A and B are phenyl, and which have a bromine content of at least 10 and in particular 20% are of particular interest.

High molecular weight-organic materials which can be coloured or pigmented with the brominated 1,4-diketopyrrolo-[3,4-c]-pyrroles of the formula I obtained according to the invention are, for example, cellulose ethers and esters, such as ethylcellulose, nitrocellulose, cellulose acetate or cellulose butyrate, natural resins or synthetic resins, such as polymerization resins or condensation resins, for example aminoplasts, in particular urea/formaldehyde and melamine/formaldehyde resins, alkyd resins and phenoplasts, polycarbonates, polyolefins, such as polyethylene or polypropylene, polystyrene, polyvinyl chloride, polyphenyl ethers, polyphenyl sulfide, polyacrylonitrile, polyacrylates, polyamides, polyurethanes or polyesters, rubber, casein, silicone and silicone resins, individually or as mixtures.

It is of no importance here whether the high molecular weight organic compounds mentioned are in the form of plastic compositions or melts or in the form of spinning solutions, varnishes, paints or printing inks. Depending on the intended use, it proves to be advantageous to employ the pigments obtained according to the invention as toners or in the form of preparations. The compounds of the formula I are employed in an amount of preferably 0.1 to 10% by weight, based on the high molecular weight organic material to be pigmented.

The resulting colourations, for example in plastics, fibres, varnishes or prints, are distinguished by a high tinctorial strength, a good dispersibility, good stability to over-varnishing, migration, heated light and weather and a high gloss and good IR reflectance.

The compounds of the formula (I) brominated according to the invention can also be used as photoconductive substances, for example in electrophotographic recording materials.

The compounds of the formula (I) brominated according to the invention can also be used as photoelectrophoretic toners.

The compounds of the formula (I) brominated according to the invention which are present in partly or completely dissolved form in the polymers used are likewise distinguished by a pure colour shade, a good tinctorial strength, good general fastness properties, in particular fastness to light and sublimation, and also a high fluorescence. They are suitable for use in solar energy collectors and for the production of laser beams.

The following examples illustrate the invention.

EXAMPLE 1

A crystallization dish with 278 g of bromine is placed on the floor of a desiccator ($\phi=20$ cm) and a crystallization dish filled with 50 g of 3,6-diphenyl-1,4-diketopyrrolo-[3,4-c]-pyrrole is placed on the porcelain insert. The lid is replaced, the venting tap is opened slightly and the system is left to stand at room temperature for 8 days. Thereafter, the crystallization dish with the brominated product is removed and left to stand to attain constant weight [in order to remove excess bromine, the product can also be added slowly to a solution of 1.5 to 3 equivalents (based on the bromine) of cyclohexane in 200 ml of carbon tetrachloride at 0°–5° C. and, after being stirred for 30 minutes, filtered with suction].

For purification, the crude product is refluxed in methanol for a few hours, filtered off with suction, washed with methanol and dried in a vacuum drying cabinet at 70° C. 67.0 g (87% of theory) of a red sparingly soluble solid which is identical to 3,6-di-(4-bromophenyl)-1,4-diketopyrrolo-[3,4-c]-pyrrole from the spectroscopic and coloristic point of view are obtained. The product gives a red coloration when incorporated into PVC.

| | C, H, N, Br analysis: | | | |
|---|---|---|---|---|
| | C | H | N | Br |
| Calculated: | 48.46% | 2.26% | 6.28% | 35.8% |
| Found: | 49.85% | 2.47% | 6.40% | 33.5% |

EXAMPLE 2

A mixture of 1.0 g of 3,6-diphenyl-1,4-diketocpyrrolo-[3,4-c]-pyrrole and 3.8 g of bromine in 10 ml of carbon tetrachloride is stirred at room temperature in a 50 ml round-bottomed flask with a reflux condenser for 18 hours. The product is filtered off with suction, washed with a large amount of carbon tetrachloride and then with methanol and subsequently refluxed in 200 ml of methanol for 3 hours, the mixture is cooled and the product is washed with methanol and dried in a vacuum drying cabinet at 70° C. 0.9 g of a pigment mixture which has a bromine content of 13.3%, according to field desorption MS analysis consists of compounds of the formulae

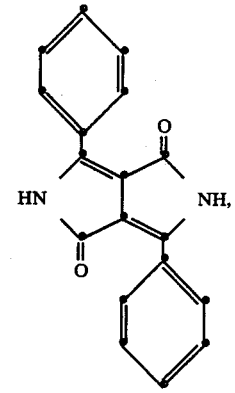

A

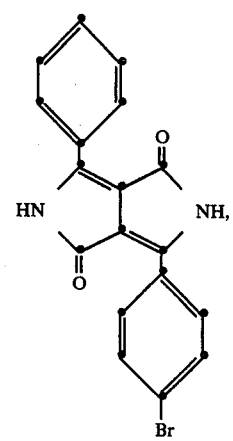

B

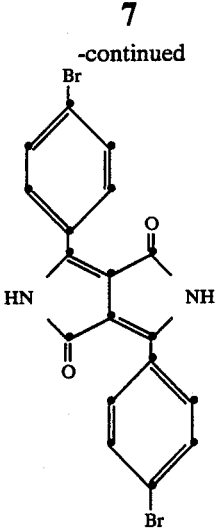

and, when incorporated into PVC, gives a red coloration is obtained.

EXAMPLE 3

55.2 g of aluminium chloride are taken in a 50 ml sulfonating flask and 3.4 g of NaCl, 2.5 g of KCl and 0.9 g of NaF are added in portions at 100° C. 2.0 g of 3,6-diphenyl-1,4-diketopyrrolo-[3,4-c]-pyrrole are added to the resulting melt and 2.4 g of bromine are then added dropwise in the course of one hour. The mixture is stirred at 100° C. for 4 hours and then poured onto 100 ml of 2 N HCl/ice and filtered. The residue is refluxed in methanol for 16 hours, the mixture is cooled and the product is filtered off with suction, washed with methanol and dried in a vacuum drying cabinet at 70° C. 2.3 g of a pigment mixture (essentially consisting of components A, B and C) which has a bromine content of 31.6% and, when incorporated into PVC, gives a red coloration are obtained.

EXAMPLE 4

3. g of 3,6-diphenyl-1,4-diketo-pyrrolo-[3,4-c]-pyrrole are added to 7.7 ml of concentrated sulfuric acid in a 100 ml round-bottomed flask. Thereafter, a solution of 8.7 g of dibromocyanuric acid in 70 ml of concentrated sulfuric acid is slowly added and the resulting mixture is stirred at room temperature for 15 minutes. The reaction mixture is then poured onto 100 ml of ice and filtered with suction. The residue is suspended in 50 ml of dilute NaOH solution, filtered off with suction, washed with water and dried in a vacuum drying cabinet. The solid is then refluxed in methanol for 3 hours. 2.1 g of a pigment mixture (essentially consisting of components A, B and C), which has a bromine content of 43.8% and, when incorporated into PVC, gives an orange coloration are obtained.

EXAMPLE 5

5.0 g of 3,6-diphenyl-1,4-diketo-pyrrolo-[3,4-c]pyrrole are introduced into a glass dish with three legs in a 1 l enamel autoclave. 27.8 g of bromine are introduced onto the bottom of the autoclave and the autoclave is sealed and heated to 100° C. for 18 hours. It is cooled to room temperature, vented and flushed with nitrogen, the glass dish is removed and, to remove excess bromine and to avoid side reactions, its contents are slowly added to a solution of 1.5 to 3 equivalents (based on the bromine) of an olefin, for example cyclohexene, in 200 ml of carbon tetrachloride at 0°–5° C., the mixture is stirred for 30 minutes and then filtered with suction and, for purification, the product is refluxed in methanol for a few hours, filtered off with suction and dried at 70° C. in a vacuum drying cabinet. 6.5 g of a solid which, when incorporated into PVC, gives a red coloration and is identical to 3,6-di(4-bromophenyl)-1,4-diketopyrrolo-[3,4-c]-pyrrole from the spectroscopic and coloristic point of view are obtained.

| | C, H, N, Br Analysis: | | | |
|---|---|---|---|---|
| | C | H | N | Br |
| Calculated | 48.46% | 2.26% | 6.28% | 35.8% |
| Found | 49.78% | 2.44% | 6.33% | 33.8% |

EXAMPLE 6

If the procedure followed is as in Example 5 but the reaction is carried out at 23° C., this gives 5. g of a pigment mixture (essentially consisting of components A, B and C) which has a bromine content of 21.8% and, when incorporated into PVC, gives a red coloration.

EXAMPLE 7

30 g of 3,6-diphenyl-1,4-diketopyrrolo-[3,4-c]-pyrrole and 116 g of bromine are stirred in 300 ml of carbon tetrachloride in a 1 l enamel autoclave at 100° C. for 18 hours. After cooling to room temperature, the suspension is filtered with suction. To remove excess bromine, a solution of, for example, 1.5 to 3 equivalents (based on the bromine) of cyclohexene in 200 ml of carbon tetrachloride is advantageously added slowly to the cooled reaction mixture at 0°–5° C., before the filtration reduction, and the mixture is stirred for about 30 minutes. For purification, the crude product is refluxed in methanol for a few hours, filtered off with suction and dried in a vacuum drying cabinet at 70° C. 36.9 g of a pigment mixture (essentially consisting of components A, B and C) which has a bromine content of 25.8% and, when incorporated into PVC, gives a red coloration are obtained.

EXAMPLE 8

If the procedure is as in Example 7 but petroleum ether 40°–60° is used as the solvent, instead of carbon tetrachloride, this gives 32.0 g of a pigment mixture (essentially consisting of components A, B and C) which has a bromine content of 19.7% and, when incorporated into PVC, gives a red coloration.

EXAMPLE 9

If the procedure is as in Example 7, but ®Shellsol TD (mixture of aliphatic hydrocarbons from Shell) is used as the solvent, instead of carbon tetrachloride, this gives 34.4 g of a pigment mixture (essentially consisting of components A, B and C) which has a bromine content of 12.5% and, when incorporated into PVC, gives a red coloration.

EXAMPLE 10

If the procedure is as in Example 7, but o-dichlorobenzene is used as the solvent, instead of carbon tetrachloride, this gives 35.5 g of a pigment mixture (essentially consisting of components A, B and C) which has a bromine content of 26.3% and, when incorporated into PVC, gives a red coloration.

EXAMPLE 11

If the procedure is as in Example 7, but nitrobenzene is used as the solvent, instead of carbon tetrachloride, this gives 26.5 g of a pigment mixture (essentially consisting of components A, B and C) which has a bromine content of 31.2% and, when incorporated into PVC, gives a red coloration.

EXAMPLE 12

If the procedure is as in Example 7, but 1,1,2,2-tetrachloroethane is used as the solvent, instead of carbon tetrachloride, this gives 36.5 g of a pigment mixture (essentially consisting of components A, B and C) which has a bromine content of 26.7% and, when incorporated into PVC, gives a red coloration.

EXAMPLE 13

3.0 g of 3,6-diphenyl-1,4-diketopyrrolo-[3,4-c]pyrrole and 11.4 g of bromine are stirred in 30 ml of carbon tetrachloride in a bomb tube (100 ml) at room temperature for 18 hours. Working up analogously to Example 2 gives 2.8 g of a pigment mixture (essentially consisting of components A, B and C) which has a bromine content of 11.1% and, when incorporated into PVC, gives a red coloration.

EXAMPLE 14

If the procedure is as in Example 14, but 0.5 g of the sodium salt of bis-2-ethylhexylsulfosuccinate are also added, this gives 3.1 g of a pigment mixture (essentially consisting of components A, B and C) which has a bromine content of 15% and, when incorporated into PVC, gives a red coloration.

EXAMPLE 15

If the procedure is as in Example 13, but 5.7 g of $K_2CO_3$ are also added, this gives 2.9 g of a pigment mixture (essentially consisting of components A, B and C) which has a bromine content of 16% and, when incorporated into PVC, gives a red coloration.

EXAMPLE 16

If the procedure is as in Example 1, but 3.0 g of 3,6-di-(4-phenyl-phenyl)-1,4-diketopyrrolo-[3,4-c]-pyrrole and 7.3 g of bromine are used as the starting material, this gives 3.7 g of a pigment mixture which has a bromine content of 35.7% and, when incorporated into PVC, gives a red-violet coloration.

EXAMPLE 17

3.0 g of 3,6-diphenyl-1,4-diketopyrrolo-[3,4-c]pyrrole are added to 30 ml of bromine and the reaction mixture is stirred at room temperature for one hour. It is filtered with suction and the residue is washed with petroleum ether, refluxed in methanol for 3 hours, filtered off with suction, washed with methanol and dried in a vacuum cabinet at 70° C. 3.2 g of a pigment mixture (essentially consisting of components A, B and C) which has a bromine content of 21.9% of Br and, when incorporated into PVC, gives a red coloration are obtained.

EXAMPLE 18

If the procedure is as in Example 1, but 0.5 g of 3,6-di-(3-methoxy)-phenyl-1,4-diketopyrrolo-[3,4-c]-pyrrole and 7.3 g of bromine are used instead of 50 g of 3,6-diphenyl-1,4-diketo-pyrrolo-[3,4-c]-pyrrole and 278 g of bromine, this gives 0.5 g of a pigment mixture which has a bromine content of 48.8% and, when incorporated into PVC, gives a red-violet coloration.

EXAMPLE 19

If the procedure is as in Example 7, but 232 g of bromine are used, this gives 40.3 g of a pigment mixture (essentially consisting of components A, B and C) which has a bromine content of 32.4% and, when incorporated into PVC, gives a red coloration.

EXAMPLE 20

If the procedure is as in Example 7, but o-dichlorobenzene is used instead of carbon tetrachloride and 232 g of bromine are used, this gives 36.7 g of a pigment mixture (essentially consisting of components A, B and C) which has a bromine content of 30.6% and, when incorporated into PVC, gives a red coloration.

We claim:

1. A mixture of at least one non-brominated and at least one uniformly or differently brominated pyrrolo-[3,4-c]-pyrrole obtained by bromination of a pyrrolo-[3,4-c]-pyrrole or a mixture of different pyrrolo-[3,4-c]-pyrroled of the formula I $$\begin{array}{c} A \quad Z \\ \diagup \diagdown \diagup \diagdown \\ HN \qquad NH, \\ \diagdown \diagup \diagdown \diagup \\ Z \quad B \end{array} \quad (I)$$

in which A and B are a group of the formula $$\begin{array}{c} R_2 \\ R_1 \diagdown \diagup R_3 \\ \diamond \end{array}$$

in which $R_1$, $R_2$ and $R_3$ independently of one another are substituents which do not interfere with the bromination, selected from the group consisting of hydrogen, halogen, nitro, amino, carbamoyl, cyano, trifluoromethyl, $C_2$–$C_{13}$-alkylcarbamoyl, $C_1$–$C_{12}$-alkyl, $C_1$–$C_{12}$-monoalkylamino, $C_2$–$C_{24}$-dialkylamino, phenyl which is unsubstituted or substituted by halogen, $C_1$–$C_{12}$-alkyl or $C_1$–$C_{12}$-alkoxy, phenoxy, phenylmercapto, phenoxycarbonyl or phenylcarbamoyl, and in which at least one of the substutuents $R_1$, $R_2$ or $R_3$ must be hydrogen, and Z is either either oxygen or sulfur, the bormination comprising the step of reacting the pyrrolo-[3,4-c]-pyrrole or the mixture of pyrrolo-[3,4-c]-pyrroles of the formula I with a brominating agent selected from the group consisting of bromine and dibromocyanuric acid in an amount which supplies 0.5 to 70 equivalents of bromine, either in a solvent or in a melt in the absence of a solvent at termperatures between $-20°$ and $200°$ C., until the desired bromine content is reached.

2. The mixture of claim 1, obtained by bromination of a pyrrolo-[3,4-c]-pyrrole of the formula I, wherein Z is oxygen.

3. The mixture of claim 1, obtained by bromination of a pyrrolo-[3,4-c]-pyrrole of the formula I, wherein A and B are each a group of the formula

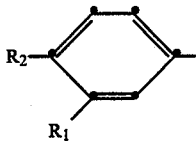

in which $R_1$ and $R_2$ are hydrogen, $C_1$–$C_4$-alkyl, $C_1$–$C_4$-alkoxy or phenyl.

4. The mixture of claim 1, obtained by bromination of a pyrrolo-[3,4-c]-pyrrole of the formula I wherein A and B are a group of the formula

in which $R_2$ is hydrogen or phenyl.

5. The mixture of claim 1, obtrained by bromination of a pyrrolo-[3,4-c]-pyrrole of the formula I, wherein A and B are identical.

6. Mixture according to claim 1, with a bromine content of at least 10%, obtained by bromination of a pyrrolo-[3,4-c]-pyrrole of the formula I in which A and B are phenyl.

7. A process for the preparation of a 3,6-di(bromophenyl)-1,4-diketopyrrolo-[3,4-c]-pyrrole comprising the step of reacting a pyrrolo-[3,4-c]-pyrrole or a mixture of different pyrrolo-pyrroles of the formula

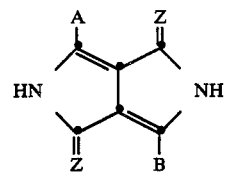

in which A and B are a group of the formula

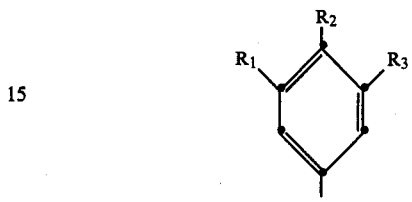

in which $R_1$, $R_2$ and $R_3$ independently of one another are substituents which do not interfere with the bromination, selected from the group consisting of hydrogen, halogen, nitro, amino, carbamoyl, cyano, trifluromethyl, $C_2$–$C_{13}$-alkylcarbamoyl, $C_1$–$C_{12}$-alkyl, $C_1$–$C_{12}$-alkoxy, $C_1$–$C_{12}$-alkylmercapto, $C_2$–$C_{13}$-alkoxycarbonyl, $C_2$–$C_{13}$-alkanoylamino, $C_1$–$C_{12}$-monoalkylamino, $C_2$–$C_{24}$-dialkylamino, phenyl which is unsubstituted or substituted by halogen, $C_1$–$C_{12}$-alkyl or $C_1$–$C_{12}$-alkoxy, phenoxy, phenylmercapto, phenoxycarbonyl or phenylcarbamoyl, and in which at least one of the substituents $R_1$, $R_2$ or $R_3$ must be hydrogen, and Z is either oxygen or sulfur, with a brominating agent selected from the group consisting of bromine and dibromocyanuric acid in an amount which supplies 0.5 to 70 equivalents of bromine, either in a solvent or in a melt in the absence of a solvent at tempertures between $-20°$ and $200°$ C., until the desired bromine content is reached.

8. The process of claim 7, wherein $R_1$ and $R_3$ are hydrogen and $R_2$ is hydrogen or phenyl.

9. The process of claim 7 wherein Z is oxygen.

10. The process of claim 7 wherein A and B are identical.

11. The process of claim 7 wherein $R_1$ and $R_2$ are hydrogen, $C_1$–$C_4$-alkyl, $C_1$–$C_4$-alkoxy or phenyl and $R_3$ is hydrogen.

12. The process of claim 7 wherein A and B are phenyl.

13. The process of claim 7 wherein the bromine is used as bromine in a solvent.

14. The process of claim 7 wherein the brominer is used as bromine without a solvent.

* * * * *